(12) United States Patent
Kimmig et al.

(10) Patent No.: US 12,278,452 B2
(45) Date of Patent: Apr. 15, 2025

(54) HEAD PART OF AN IMPLANTABLE DEVICE, METHOD FOR PRODUCING THE HEAD PART AS WELL AS A PLUG ASSEMBLY WHICH CAN BE FITTED INTO THE HEAD PART

(71) Applicant: Neuroloop GmbH, Freiburg (DE)

(72) Inventors: Fabian Kimmig, Freiburg (DE); Tim Boretius, Freiburg (DE)

(73) Assignee: NEUROLOOP GMBH, Freiburg (DE)

( * ) Notice: Subject to any disclaimer, the term of this patent is extended or adjusted under 35 U.S.C. 154(b) by 439 days.

(21) Appl. No.: 17/908,966

(22) PCT Filed: Apr. 9, 2021

(86) PCT No.: PCT/EP2021/059291
§ 371 (c)(1),
(2) Date: Sep. 2, 2022

(87) PCT Pub. No.: WO2021/219344
PCT Pub. Date: Nov. 4, 2021

(65) Prior Publication Data
US 2023/0106271 A1    Apr. 6, 2023

(30) Foreign Application Priority Data
Apr. 28, 2020  (DE) .................... 10 2020 205 350.2

(51) Int. Cl.
*H01R 24/58* (2011.01)
*H01R 13/02* (2006.01)

(52) U.S. Cl.
CPC ............ *H01R 24/58* (2013.01); *H01R 13/02* (2013.01); *H01R 2201/12* (2013.01)

(58) Field of Classification Search
None
See application file for complete search history.

(56) References Cited

U.S. PATENT DOCUMENTS 5,782,892 A * 7/1998 Castle ................. A61N 1/3752
607/10
6,390,843 B1    5/2002 Lim
(Continued)

FOREIGN PATENT DOCUMENTS

DE    102012010901    12/2012
DE    202013012073    3/2015
(Continued)

OTHER PUBLICATIONS

International Search report for PCT/EP2018/081922 ; mailed Jan. 31, 2019; 22 pages.
(Continued)

*Primary Examiner* — Tho D Ta
(74) *Attorney, Agent, or Firm* — Fitch, Even, Tabin & Flannery LLP

(57) ABSTRACT

The invention pertains to a head part of an implantable device, its method of production and a plug assembly which can be fitted into the head part. The head part comprises a head part housing which has at least one blind hole plug contact socket with a socket opening and a socket base axially opposite the socket opening, along which at least one electrically conductive contact ring element and an electrically insulating, elastically deformable seal ring is positioned and which are enclosed by a solidified casting compound, are joined together in a coaxial arrangement and in an axially serial sequence.

19 Claims, 1 Drawing Sheet

(56) References Cited

U.S. PATENT DOCUMENTS

| | | |
|---|---|---|
| 8,267,708 B1 | 9/2012 | Sochor |
| 8,527,054 B2 * | 9/2013 | North .................. A61N 1/3754 607/38 |
| 8,742,268 B2 * | 6/2014 | Reisinger ........... H01R 13/5224 361/679.1 |
| 10,471,251 B1 | 11/2019 | Manicka |
| 2003/0018364 A1 | 1/2003 | Belden |
| 2005/0043765 A1 | 2/2005 | Williams |
| 2008/0077190 A1 | 3/2008 | Kane |
| 2008/0234778 A1 * | 9/2008 | Rebentisch ........ H01R 13/5224 607/36 |
| 2011/0004279 A1 | 1/2011 | North |
| 2012/0245657 A1 * | 9/2012 | Lim .................... H01R 13/639 607/72 |
| 2013/0035730 A1 * | 2/2013 | Erickson ............. H01R 13/639 29/857 |
| 2013/0245710 A1 | 9/2013 | Foster |
| 2014/0237806 A1 | 8/2014 | Smith |
| 2015/0142092 A1 | 5/2015 | Vadlamudi |
| 2016/0100887 A1 | 4/2016 | Wu |
| 2020/0077953 A1 | 3/2020 | Manicka |

FOREIGN PATENT DOCUMENTS

| | | |
|---|---|---|
| DE | 102017222364 | 6/2019 |
| DE | 102018124307 | 4/2020 |
| EP | 2134418 | 12/2009 |
| WO | 2018222973 | 12/2018 |
| WO | 2019115176 | 6/2019 |

OTHER PUBLICATIONS

DE102012010901 machine translation.
DE102017222364 machine translation.
DE202013012073 machine translation.
WO2019115176 machine translation.
Communication, International Search Report and Written Opinion for PCT/EP2021/061682, mailed Aug. 10, 2021, 12 pages.

* cited by examiner

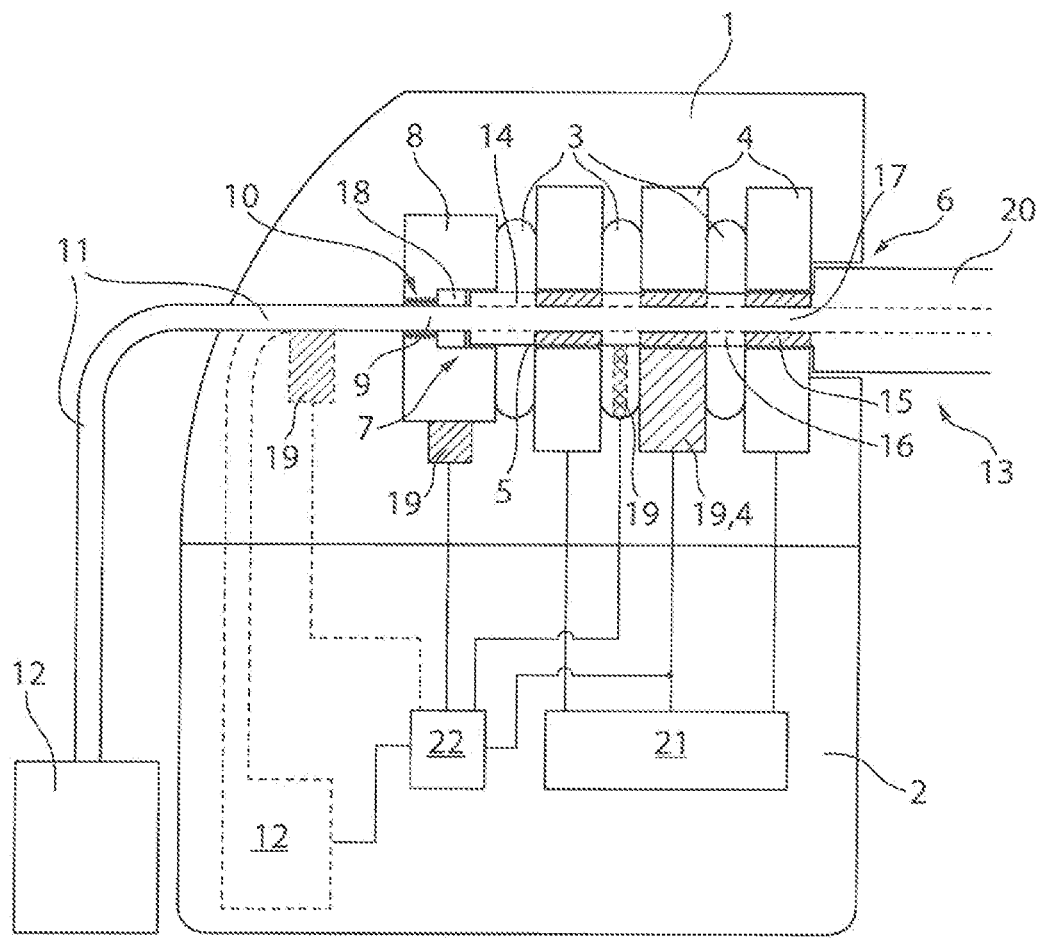

HEAD PART OF AN IMPLANTABLE DEVICE, METHOD FOR PRODUCING THE HEAD PART AS WELL AS A PLUG ASSEMBLY WHICH CAN BE FITTED INTO THE HEAD PART

CROSS REFERENCE TO RELATED APPLICATIONS

Reference is made to PCT/EP2021/059291, filed Apr. 9, 2021, and German Application No. 10 2020 205 350.2, filed Apr. 28, 2020, which are incorporated herein by reference in their entirety.

BACKGROUND OF THE INVENTION

Field of the Invention

The invention relates to a head part of an implantable medical device, its method of production and a plug assembly which can be fitted into the head part. The head part comprises a head part housing which has at least one blind hole-type plug contact socket with a socket opening as well as a socket base lying axially opposite the socket opening, along which at least one electrically conductive contact ring element and an electrically insulating, elastically deformable seal ring, which are enclosed by a solidified casting compound, are joined together in a coaxial arrangement and in an axially serial sequence.

Description of the Prior Art

Implantable medical devices for the purpose of the electrical stimulation of local intracorporeal tissue or nerve areas, in short implantable pulse generators (IPG), for example for cardiac treatment, defibrillation, and pacemakers as well as resynchronisation applications, for neurostimulation measures, such as spinal cord simulation, brain stimulation or vagus nerve stimulation to name but a few, as a general rule comprise a self-contained housing which contains components for electrical pulse generation and at least one electrical energy source and an electrical circuit structure connected thereto. In addition, adjoining the housing is a so-called head part, which contains an electrical contact arrangement connected to the energy supply and the electrical circuit structure, into which a socket assembly, which closes the head part in a fluid-tight manner, can be fitted, and is contacted with electrical supply and discharge lines for the purpose of intracorporeal local application of electrical stimulation signals, as well as, if necessary, the supply of intracorporeally locally picked up electrical signals to the electrical circuit structure present in the housing.

Described in document EP 2 134 418 B1 is a head part of an implantable medical device of the type in question which along a joining seam comprises two head part housing halves that can be joined together and into which in serial sequence semi-cylindrical recesses are introduced that are separated by intermediate walls and into which electrically conductive contact ring elements and electrically insulating sealing rings are inserted each in serially alternating order. The head part therefore comprises an arrangement of electrically insulated contact ring elements that are coaxially orientated with regard to each other, for the electrical contacting of which a lateral access is provided in the head part through which an electrical plug assembly can be inserted in a fluid-tight manner into a hollow space enclosed by all annular contact ring elements.

Document DE 10 2012 010 901 A1 discloses a method for positioning and holding electrical contacts and seals within a head part for electrically contacting a medical implantable device. A blind hole base is introduced into one side of the head part housing made of a biocompatible and electrically insulating material, into which electrically conductive and annular sealing elements are inserted in alternating sequence which jointly enclose a hollow space into which a pin plug assembly can be fitted. Within the head part, each of the annular contact rings is connected by way of an electrical connection line to electrical components located within the housing of the medical implantable device.

Disclosed in DE 20 2013 012 073 U1 is a plug boring module assembly, for the assembly of contact rings and sealing elements arranged in alternating order along a pin shaped assembly tool. By use of a clamping device, all contact rings and sealing elements arranged along the assembly tool are clamped to each other through the application of an axial joining force. A sleeve element is used for conserving a joining force which is mounted with a grub screw in an axially fixed manner on the assembly tool, which together with an assembly tool head at the end, the arrangement of contact rings and sealing elements on both sides is axially deliminated. In the clamped state, the arrangement is cast in a hardenable casting compound, which where solidified takes up the joining force.

In place of a grub screw as the fixing aid at the end for conserving the axial joining force acting on the sequence of contact rings and sealing ring elements arranged along the pin-like assembly tool, in document WO 2019/115176 A1 use of an assembly plate is disclosed which is provided with an opening and internal thread which is inserted into the internal thread opening. The pin-like assembly tool is inserted with an external thread arranged on its end.

Document US Patent Publication 2008/0077190 A1 discloses a head part for the electrical connection to a medical implant, into which a plug unit can be fitted in a fluid-tight manner. In addition to the contact electrodes provided on the plug and head part, in an optical transmission channel is provided in each of the two components. Both components are fitted into each other to be optically coupled to each other to transmit optical signals.

SUMMARY OF THE INVENTION

The invention modifies a head part of an implantable medical device, its method of production and a plug assembly fitted into the head part so that in addition to the previously known generation, transmission and application of electrical stimulation signals, the functional scope of implantable pulse generators (IPG) is increased without significantly changing their size.

The head part according to the invention is for an implantable medical device with a head part housing which has at least one blind hole-type plug contact socket with a socket opening, and a socket base axially opposite the socket opening, along which are at least one electrically conductive contact ring element and an electrically insulating, elastically deformable seal ring, which are enclosed by a solidified casting compound, are joined together in a coaxial arrangement and in an axially serial sequence. The socket base is delimited by a connection, which at least is partially enclosed by the solidified casting compound and is attached to at least one media channel opening into the blind hole plug contact socket which is at least partially enclosed by the solidified casting compound and comprises a channel end facing away from the connection and is connected to a media source. The at least one media channel is a fluid line. Preferably the media source is connected to a fluid pump, which preferably is connected to a fluid reservoir. Alternatively, instead of being connected to a media source, the media channel is connected to a media sink, along which is an active fluid conveyor with at least one collecting vessels.

The invention uses the opening in the assembly plate provided with an internal thread described in aforementioned document WO 2019/115176 A1. After removal of the assembly tools from the completed head part, this opening which otherwise has no function, directs a media flow of any kind through the opening. The assembly plate, which in the aforementioned prior art can be considered as a type of lost component which is completely enclosed by the casting compound of the head part which within the solidified casting compound there otherwise is no function for the further operation of the head part. The implantable pulse generator (IPG) connected to the head part, forms the central component of the modified head part according to the invention, which in addition to the stated function as a coupling opening, through which a media flow can be directed, also serves as a mechanical holding or supporting structure for applying a media channel at the end.

The media channel, which in the simplest form of invention is designed as a hollow channel, ends at one side at the assembly plate, which hereinafter is referred to as connection, retains its original function as an auxiliary component to generate an axial joining force through the provision of an inner thread as previously described.

The media channel starting from the connection is surrounded by the casting compound of the head part which in a preferred embodiment projects out through the head part as a continuing hollow line with an end connected to a media source. In a first embodiment, the media channel outside the head part, as well as the media source connected at the end with the media channel, are separate from the head part and an implantable medical device directly adjoining, in which a pulse generator is contained. Alternatively, a further example of embodiment integrates the implantable medical device of the media channel and the media source connected thereto.

The media channel leading into and out of the head part, and the media source connected at one end with the media channel, is designed for the type of medium.

The media channel is designed as a fluid channel, for a gaseous or liquid medium which flows in the media channel in a fluid-tight manner from the media source. The media source may be configured as a fluid reservoir, preferably supported by a fluid conveying unit which is combined with the fluid reservoir as a structural unit or is arranged along the media channel, in the direction of the blind hole plug contact socket into which the media channel opens.

In combination with the above embodiment, the media channel, along which a light conducting fluid flows, preferably also acts as a light guide. Also acting as a media source which in this case is a light source that emits light which is guided via the light guide running along the media channel to the light guide end which is opens into the blind hole plug contact socket.

For mechanically robust positioning of the media channel connected at the end to the connection, the connection has a joint contour enclosing the media channel opening into the blind hole plug contact socket in which a second media channel is within the plug contact socket that is connected to the media channel opening into the blind hole-plug contact socket. The second media channel is part of an implantable plug assembly d according to invention for joining into the blind hole plug contact socket of the aforementioned head part. The plug assembly comprises a plug body with at least one interior hollow channel corresponding to the aforementioned second media channel with one side opening to a distal plug body end. The distal plug body end has a joint contour which when the plug assembly is fitted therein ensures a flush transition of the hollow channel to the media channel opening into blind hole plug contact socket. As a result loss-free coupling is possible and further the conveying or transfer of the medium from the first media channel into the hollow channels enable a second media channel.

The implantable plug assembly is designed in manner known to transmit electrical signals and in the longitudinal extension of the plug has a serial sequence of plug contact rings and sealing rings or electrical insulation rings corresponding to a number and arrangement of the electrical contact ring elements and sealing rings along the plug assembly contact socket.

In the joined state of the implantable plug assembly within the plug contact socket of the head part side, the electrical functionality of the implantable device for the application of electrical stimulation signals is retained in spite of a modified head part and a modified plug assembly. The additional media channel on the head side and plug side leading off with the discharging electrical line, or separately therefrom, provides an additional intracorporeal locally applicable media output, for example in the form of a gas or liquid flow, or in combination with additional light transmission.

In a further preferred embodiment, at least one sensor is integrated within the head part along the media channel, which is at least in part enclosed by the solidified casting compound, which can detect, or sensorily record, the medium conveyed within the media channel at least quantitatively in terms of the conveyed volume, conveyed rate or light intensity. Depending on the type and design of the at least one sensor, within the head part along the media channel, an electrical or mechanically connection of the at least one sensor may be made to at least one electrically conducting contact ring element applied within the head part. Sensors from the following group may be: ultrasonic, optical, pressure, Hall effect, flow, needle, fluorescence, pressure etc.

The at least one sensor arranged along the media channel is preferably connected to an electrical energy source which supplies electrical energy to the pulse generator within the medical device. Furthermore, the at least one sensor is connected to an evaluation and control unit, which is connected to at least one of an additional memory unit and the media source. In this way it is possible to record the actual status of the medium flowing or being conveyed along the media channel and to control or regulate the media source as function of the actual status.

The head part assembled according to the invention as well as the functionally modified plug assembly for the additional transmission of a medium in the form of a fluid, preferably and of a light flow, does not change the shape and size from the used and known medical implants, but significantly expands the functionality and the therapeutic mode of action of comparable implants associated therewith. In addition to the electrical stimulation of at least one intracorporeal local tissue and nerve areas, it is therefore also possible to apply a fluid, and, if necessary, light.

Through the combined use of the connection acting as an assembly plate providing a supporting structure, as well as for the connection flange for two media channels adjoining each other in an abutting manner, an innovative method of manufacturing such a head part is achieved. Thus, in a first processing step, the connection serves as a supporting plate in a conventional manner together with the at least one contact ring element as well as the at least one sealing ring, along a rod-shaped assembly tool, and along the rod-shaped assembly tool these are joined to each other in a positive manner through the generation of an axial clamping force.

In a next step, the media channel, in the form of a hollow line or hollow cannula is connected at its end with the connection in such a way that the media channel adjoins directly or indirectly at the opening within the connection. For example, the media channel can be precisely fitted to enclose the end of the rod-shaped assembly tool projecting at the rear on the connection.

Subsequent to this, the connection is arranged and positively joined along the rod-shaped assembly tool. Then the at least one contact ring element and the at least one sealing ring and the at least one media channel is directly or indirectly applied to the connection means is at least partially surrounded by a hardenable casting compound that is present in flowable form. The rod-shaped assembly tool is then released and removed from the connection. The at least one contact ring element and the least one sealing ring after solidification of the casting compound forms a dimensionally stable matrix of at least one part of the head part housing, which absorbs the axial joining force. By removing the assembly tool, the media channel applied directly or indirectly on the connection opens at one side into the blind hole plug contact socket of the head part formed by removing the assembly tool.

BRIEF DESCRIPTION OF THE DRAWING

The invention will be described below without restricting the general inventive concept by way of examples in the drawing.

The drawing Illustrates a head part of an implantable pulse generator combined with an additional media channel with an appropriately configured plug assembly.

DETAIL DESCRIPTION OF THE INVENTION

The drawing shows a schematic view of a head part 1 combined with an implantable, medical device 2 which is a pulse generator forming a component. Arranged in an axially serial sequence in the head part 1 made of a hardenable casting compound are alternating electrically insulating, electrically deformable sealing rings 3 and electrically conducting contact ring elements 4. The sealing rings 3 and the electrical contact ring elements 4 enclose a blind hole plug contact socket 5 which has a socket opening 6 that is accessible on the outer wall of the head part 1. The socket base 7 opposite the socket opening 6, is delimited by a connection 8 that, for the production of the head part 1 and in particular for axially lining up the sealing rings 3 as well as electrical contact ring elements 4, serves as a mechanical abutment for an assembly tool used for assembly. For this, the connection 8 has an opening 9, along which, at least in parts, an internal thread 10 is incorporated.

Fitted to or in the connection 8 in the area of the opening 9 is a media channel 11, which opens into the blind hole plug contact socket 5. The media channel 11 extends, within the head part 1 and is thus enclosed by the solidified casting compound of the head part 1. The media channel 11 is a hollow channel, projecting laterally from the head part 1 and at the end is connected with a media source 12. The media source 12 is, for example, a media reservoir, from which the medium, for example gas or a liquid, is conveyed in a controlled manner by a conveying unit along the medial channel 11. In this case the media channel 11 has a hollow channel through which the gaseous or liquid medium is conveyed in the direction of the head part 1 in as loss-free a manner as possible.

The media source 12 can also be a light source. In this case, a fluid that is as transparent to light as possible, is to be conveyed through the media channels 11, which also constitutes a type of light guide, along which fluid and light from the combined media source 12 of fluid and light is conveyed in the direction of the head part 1 which is largely free of loss.

Fitted into the blind hole plug contact socket 5 is also a plug assembly 13 finished in accordance with the invention which comprises a plug body 14, having dimensions and the shape of the plug contact socket 5, on the outer perimeter on which corresponding counter contact elements 15 are arranged corresponding to the arrangement of the electrical contact ring elements 4. Between the counter contact elements 15, electrically insulating plug body areas 16 are provided. With regard to the electrical contact of the plug contact assembly 13 within the blind hole plug contact socket 5 of the head part 1, the device illustrated does not differ from comparable plug assemblies of the type in question.

According to the invention, the plug contact assembly 13 has a second media channel 17 that centrally projects through the plug body 14 and in an area of the socket base 7 flushly adjoins the medial channel 11 opening into the blind hole plug contact socket 5 as an abutment. Depending on the type and design of the media channel 11, 17, the media channel 11 on the head side and the second media channel 17 on the plug side should be connected for low-loss or loss-free connection and transmission of the respective medium. For this, at least one of an additional sealing and joint contour 18 is optionally introduced within the connection means 8 to ensure a seamless transition between the media channels 11 and 17.

Along at least one of the media channel 11 and 17, a sensor 19 is optionally arranged within the head part 1 for at least one of detecting and monitoring the medium being conveyed along the media channel 11, 17. Depending on the type and design of the sensor 19, it is directly arranged along, or integrated into, the medial channel 11, on the connection 8, on at least one of the sealing rings 3 or on at least one of the electrical contact ring elements 4. The type and application of the at least one sensor 19 is determined from the medium being transmitted along the media channel 11, 17, which for example may be gas, liquid and possibly light. The sensor 19 an be suitably selected from the following sensor types: Hall effect, optical, flow, ultrasonic, temperature, pressure sensor etc.

The plug contact assembly 13 is connected to a discharging line 20, and in addition to at least one of an electrical line, comprising the discharging media channel 17. Via the discharging media channel 17, the medium can be applied in a controlled manner for dosed therapeutic purposes at selected intracorporeal areas.

The illustrated example shows a media channel 11 leading from the head part, which separately to the IPG 2, is connected to a media source 12. It is also possible to guide the media channel 11 within the head part 1 as well as the IPG 2 and connected it to a media source arranged within the IPG, as shown by the dashed line.

Within the implantable medical device 2 designed as a pulse generator, in addition to the components 21 required for pulse generation, is an evaluation and control unit 22 connected to the at least one sensor 19 has at least one sensor signal generates a control or regulating signal to influence the media source 12. In this way, at least one of the flow and intensity of the material directed through the media channel 11, 17 can be influenced.

LIST OF REFERENCE NUMBERS

1 Head part
2 Implantable medical device designed as a pulse generator IPG
3 Sealing ring
4 Electrical contact ring element
5 Blind hole plug contact socket
6 Socket opening
7 Socket base
8 Connection means
9 Opening
10 Inner thread
11 Media channel
12 Media source
13 Plug contact assembly
14 Plug body
15 Counter contact element
16 Insulating intermediate area
17 Second media channel
18 Sealing joint contour
19 Sensor
20 Discharge line
21 Electrical components of the IPG
22 Evaluation and control unit

The invention claimed is:

1. A part for use in an implantable medical device, comprising:
   a head including a housing with at least one blind hole plug contact socket with a socket opening, a socket base axially opposite the socket opening including at least one electrically conductive contact ring element and an electrically insulated elastically deformable sealing ring which are enclosed by a solidified casting compound, the at least one electrically conductive contact ring and the electrically insulated elastically deformable sealing ring are joined coaxially in a serial sequence;
   each socket base is delimited by a connection at least partially enclosed by the solidified casting compound and attached to at least one media channel opening into the blind hole plug contact socket and comprises a channel end facing away from the connection which is connected to a media source; and
   the at least one media channel is a fluid line.

2. A part according to claim 1, wherein:
   the connection comprises a contour encompassing the media channel which opens into the blind hole plug socket including a second media channel within the plug contact socket which is connectable to the media channel opening into the blind hole plug contact socket.

3. A part according to claim 1, wherein:
   the media source is a fluid pump connected to a fluid reservoir or is a media sink.

4. A part according to claim 3, the media channel projects outwardly through and outside of the housing and is connected to the media source.

5. A part according to claim 1, wherein each media channel projects outwardly through and outside of the housing and is connected to the media source.

6. A part according to claim 1, comprising:
   at least one sensor positioned for recording information sensed from a medium present within the media channel and the at least one media channel is at least partially enclosed by the solidified casting compound.

7. A part according to claim 6, wherein:
   the at least one sensor is one of an ultrasonic, an optical, a pressure, a Hall sensor, or a flow sensor.

8. A part according to claim 6, wherein:
   the at least one sensor is one of an evaluation unit and a control unit connected to at least one of a memory and a media source.

9. A part according to claim 6, wherein:
   the at least one sensor is an electrical sensor and is mechanically connected to the at least one electrically conducting contact ring.

10. A part according to claim 9, wherein:
    the at least one sensor is one of an ultrasonic, an optical, a pressure, a Hall sensor, or a flow sensor.

11. A part according to claim 3, comprising:
    at least one sensor positioned for recording information sensed from a medium present within the media channel and the at least one media channel is at least partially enclosed by the solidified casting compound.

12. A part according to claim 11, wherein:
    the at least one sensor is one of an evaluation and control unit connected to at least one of a memory and a media source.

13. A part according to claim 5, comprising:
    at least one sensor positioned for recording information sensed from a medium present within the media channel and the at least one media channel is at least partially enclosed by the solidified casting compound.

14. A part according to claim 13, wherein:
    the at least one sensor is one of an evaluation unit and a control unit connected to at least one of a memory and a media source.

15. A part according claim 1, wherein:
    the housing is mechanically and electrically connected to an implantable pulse generator.

16. A part according to claim 15, wherein:
    the media source is integrated into the implantable medical device.

17. An implantable plug assembly for insertion into the blind hole plug contact socket within the part in accordance to claim 1, wherein:
    the plug assembly comprises a body having at least one interior hollow channel which has an opening at an end of a body of a distal plug; and
    the body of the plug assembly has an end including a connection with a contour which, when the plug assembly is within the blind hole plug contact socket, is a flush connection of the hollow channel to the media channel opening into a blind hole plug contact socket.

18. A plug assembly according to claim 17, wherein:
    the hollow channel includes a media channel opening into the blind hole plug contact socket.

19. A method of producing an implantable medical device comprising a head including a housing with at least one blind hole plug contact socket with a socket opening, a socket base axially opposite the socket opening including at least one electrically conductive contact ring element and at least one of an electrically insulated elastically deformable sealing ring which are enclosed by a solidified casting compound, the at least one electrically conductive contact ring and the electrically insulated elastically deformable sealing ring are joined coaxially in a serial sequence, each socket base is delimited by a connection at least partially enclosed by the solidified casting compound and attached to at least one media channel opening into the blind hole plug contact socket and comprises a channel end facing away from the connection which is connected to a media source, and the at least one media channel is a fluid line, the method comprising:

arranging the at least one electrically conductive contact ring and the at least one electrically insulated elastically deformable sealing ring along a rod-shaped assembly tool;

applying a force to connect the at least one contact ring and the at least one electrically insulated elastically deformable sealing ring to connect the at least one contact ring and the at least one deformable sealing ring;

enclosing at least partially the connection of at least one electrically conductive contact ring and the at least one electrically insulated elastically deformable sealing ring with a flowable casting compound that solidifies; and releasing the rod-shaped assembly tool from the connection while retaining an axial connection resulting from an applied force to form at least one part of the head.

* * * * *